United States Patent [19]

Bomsztyk

[11] Patent Number: 4,816,131

[45] Date of Patent: Mar. 28, 1989

[54] PH/$P_{CO2}$ $P_{O2}$ ELECTRODE

[75] Inventor: Karol Bomsztyk, Mercer Island, Wash.

[73] Assignee: The Board of Regents of the University of Washington, Seattle, Wash.

[21] Appl. No.: 102,323

[22] Filed: Sep. 29, 1987

[51] Int. Cl.[4] .............................................. G01N 27/30
[52] U.S. Cl. .................................... 204/403; 128/635; 204/412
[58] Field of Search ................. 128/635; 204/412, 403

[56] References Cited

U.S. PATENT DOCUMENTS

| | | | |
|---|---|---|---|
| 3,436,329 | 4/1969 | Kahn et al. | 204/403 |
| 3,666,651 | 5/1972 | Makabe | 204/420 |
| 3,726,777 | 4/1973 | Macur | 204/403 |
| 3,743,591 | 7/1973 | Steinhardt | 204/417 |
| 3,835,010 | 9/1974 | Levins | 204/417 |
| 3,900,382 | 8/1975 | Brown | 204/403 |
| 3,957,613 | 5/1976 | Macur | 204/412 |
| 4,274,418 | 6/1981 | Vesterager et al. | 128/635 |
| 4,312,734 | 1/1982 | Nichols | 204/420 |
| 4,339,317 | 7/1982 | Meiattini et al. | 204/400 |
| 4,444,644 | 4/1984 | Hiramoto et al. | 204/406 |
| 4,536,274 | 8/1985 | Papadakis et al. | 204/433 |

OTHER PUBLICATIONS

Karol Bomsztyk et al., The American Physiological Soc., pp. F933–F397, (1986).

Primary Examiner—G. L. Kaplan
Attorney, Agent, or Firm—Christensen, O'Connor, Johnson & Kindness

[57] ABSTRACT

A double and triple barrel electrode for the simultaneous measurement of pH and $P_{CO2}$; and pH, $P_{CO2}$ and $P_{O2}$ employing a membrane in conjunction with a pH fluid and fluids responsive to $CO_2$ and $O_2$. The responsive fluids exhibit a pH change upon a change in the concentration of the particular analyte in the responsive fluid. The liquid membrane is selectively permeable to $H^+$ ion, and permeable to $CO_2$ and $O_2$ gas.

44 Claims, 2 Drawing Sheets

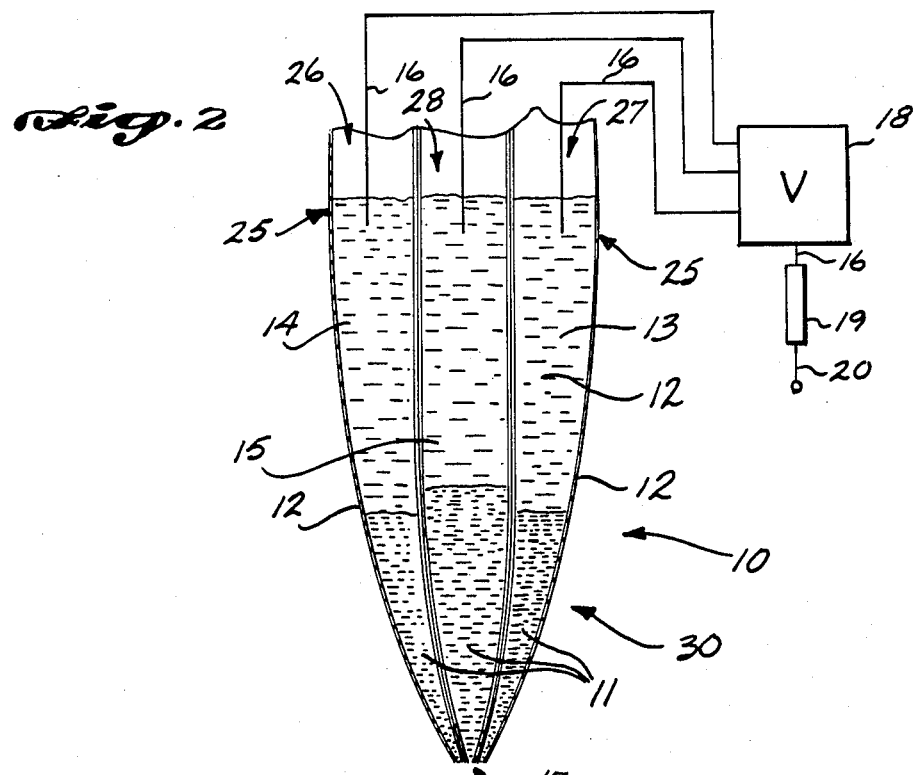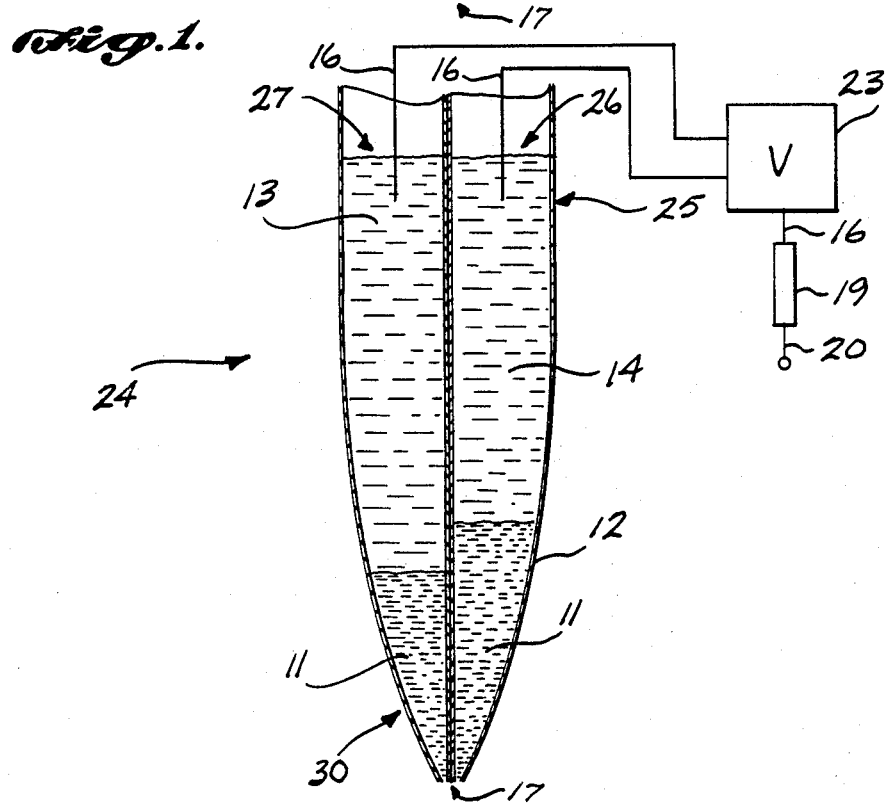

PH/$P_{CO_2}$ $P_{O_2}$ ELECTRODE

BACKGROUND OF THE INVENTION

The present invention relates to electrodes useful for measuring properties of fluids, particularly body fluids. The present invention is particularly concerned with a microelectrode capable of simultaneously measuring the pH, $P_{CO_2}$, and $P_{O_2}$ of body fluids.

Various types of electrodes have been introduced in the past to measure pH, $P_{CO_2}$ and $P_{O_2}$. The first pH-sensitive electrode used in biological applications was a miniature platinum-hydrogen electrode. This electrode suffered from several disadvantages that included very slow response time, and a voltage response which was sensitive to partial pressure of hydrogen and several oxidizing agents.

An antimony-based electrode has been used to measure the pH in chicken eggs. This electrode works by the occurrence of an oxidation-reduction reaction on a thin layer of antimonous oxide on the electrode surface. Drawbacks associated with this electrode include a pH sensitive reaction, which is not completely reversible, a voltage response which is temperature dependent and a requirement that calibration solutions be used which closely resemble the ionic composition of the systems studied. In view of the difficulties associated with metal electrodes, in the past 20 years pH-sensitive glass electrodes have become very popular.

pH-sensitive glass has been used to fabricate pH microelectrodes. Numerous improvements have been made to these glass pH microelectrodes with one of the most important improvements being introduction of the recess tip pH microelectrode. These microelectrodes work well for both intra and extra cellular pH measurements, unfortunately these microelectrodes are difficult to fabricate.

$P_{CO_2}$ microelectrodes are available, which consist of an outer glass pH-insensitive shell into which a glass membrane pH electrode is placed in a weak bicarbonate solution behind a carbon dioxide permeable silicone rubber in the electrode tip. The $P_{CO_2}$ is thus measured, as a pH change of the filling bicarbonate solution caused by the migration of $CO_2$ into the bicarbonate solution through the $CO_2$ permeable silicone rubber. This electrode works well in tissue/body fluids but is also very difficult to fabricate. An antimony microelectrode has also been used to measure the $P_{CO_2}$ of body fluids, but this electrode also suffers from all the inherent difficulties of the antimony pH electrode discussed above, in addition to the difficulty involved in fabricating such electrode.

Because the pH, $P_{CO_2}$, and $P_{O_2}$ are of vital importance to organ functions, a microelectrode device which is capable of simultaneously measuring all three parameters would have a wide application in research medicine. It could be used to monitor the tissue properties while studying an organ's susceptibility to injury induced by decreased blood flow. Such determinations would be useful in studies such as those related to acute renal failure, a major cause of kidney shutdown in hospitalized patients. Also, electrodes capable of simultaneously measuring the pH, $P_{CO_2}$ and $P_{O_2}$ would be useful in other fluid analysis such as water pollution monitoring and general chemical analysis.

Furthermore, development of a microelectrode device would have a very wide application in clinical medicine. It could be used to perform in vivo determinations of the level of blood gases presnt in arterial blood. This would avoid the need to draw blood in order to make the measurement, a problem that becomes very significant in critically ill patients who cannot afford to lose a lot of blood due to frequent arterial blood gas tests. It would be desirable to make the microelectrode so simple that it could potentially be developed into a disposal arterial blood gas device. Instead of drawing blood from an artery into a disposable syringe, as it is presently done, the arterial blood gas levels could be determined directly in the artery or tissue without any blood loss. The microelectrode device could then be discarded if there is no need for continuous monitoring.

Therefore, the need exists for an electrode capable of simultaneously measuring the pH, $P_{CO_2}$, and $P_{O_2}$ of fluids, particularly a microelectrode capable of monitoring body fluids. It is desirable that such electrodes be easy to fabricate and also be produced from materials which would allow for the disposability of such electrode device after it has been used.

SUMMARY OF THE INVENTION

The present invention is an electrode device capable of simultaneously measuring pH and $P_{CO_2}$ of fluids. The device includes a pH sensor, that contains a hydrogen ion and carbon dioxide gas permeable membrane in intimate contact with a hydrogen ion responsive fluid. The hydrogen ion responsive fluid is capable of being placed in intimate contact with a device for measuring the voltage signal from the pH sensor. The electrode device also includes a $P_{CO_2}$ sensor that contains the same hydrogen ion and carbon dioxide gas permeable membrane as the pH sensor in intimate contact with a carbon dioxide responsive fluid. The carbon dioxide responsive fluid is capable of being placed in intimate contact with a device for measuring the voltage signal from the $P_{CO_2}$ sensor. The pH sensor and the $P_{CO_2}$ sensor are intimately disposed in relationship to each other.

In another aspect, the present invention is an electrode device for simultaneously measuring the pH, $P_{CO_2}$, and $P_{O_2}$. The device includes a pH sensor which contains a hydrogen ion, carbon dioxide gas, and an oxygen gas permeable membrane in intimate contact with a hydrogen ion responsive fluid. The hydrogen ion responsive fluid is capable of being placed in intimate contact with a device for measuring the volage signal from the pH sensor. The device further includes a $P_{CO_2}$ sensor that contains the same membrane as the pH sensor in intimate contact with a arbon dioxide responsive fluid. The carbon dioxide responsive fluid is capable of being placed in intimate contact with a device for measuring the voltage signal from the $P_{CO_2}$ sensor. Additionally, the electrode device includes a $P_{O_2}$ sensor that contains the same membrane as the pH sensor and the $P_{CO_2}$ sensor, in intimate contact with an oxygen responsive fluid. The oxygen responsive fluid is capable of being placed in intimate contact with a device for measuring the voltage signal from the $P_{O_2}$ sensor. The pH sensor, $P_{CO_2}$ sensor and the $P_{O_2}$ sensor are intimately disposed in relationship to each other.

In a preferred embodiment, the electrode devices of the present invention are microelectrodes. Thus, the present invention provides an electrode device capable of simultaneously measuring the pH, $P_{CO_2}$, and $P_{O_2}$ of fluids, particularly body fluids. The electrodes are easily fabricated and may be produced from materials which allow for the disposability of such electrode devices after they have been used. The electrodes provide a simple and accurate method of measuring properties of fluids both in vitro and in vivo.

BRIEF DESCRIPTION OF THE DRAWINGS

The present invention will become more apparent from the following description thereof when considered together with the accompanying drawings. Such drawings are set forth as being merely illustrative of preferred embodiments of the present invention and are not intended in any way to be limitative thereof. It is to be understood that modifications and changes to the preferred embodiments of the invention herein described and shown can be made without departing from the spirit and scope of the invention.

FIG. 1 is a schematic illustration of a microelectrode in accordance with the present invention capable of simultaneously measuring the pH, $P_{CO2}$ and $P_{O2}$ of body fluids.

FIG. 2 is a schematic illustration of another embodiment of a microelectrode in accordance with the present invention capable of simultaneously measuring the pH and $P_{CO2}$ of body fluids.

DETAILED DESCRIPTION OF THE INVENTION

Figure 3:
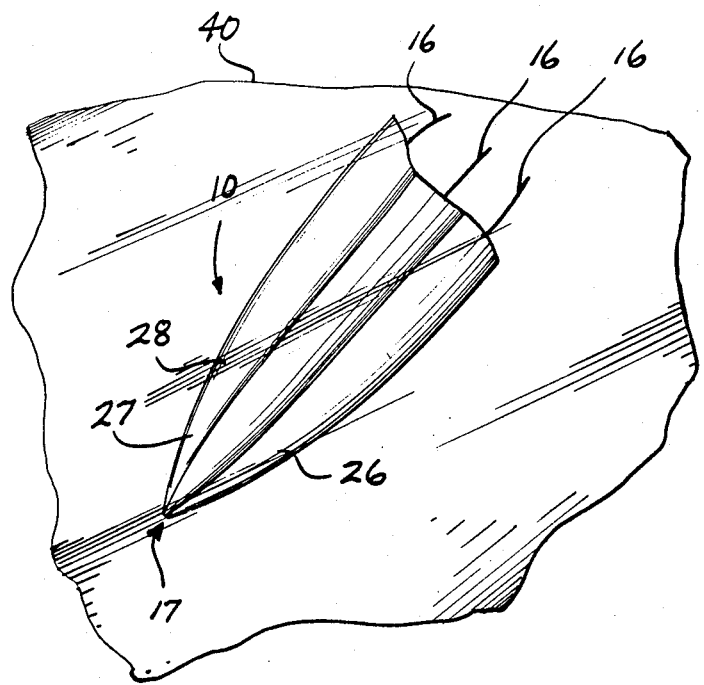
FIG. 3 is a schematic illustration of the microelectrode in accordance with the present invention packaged in a kit.

While the following description refers to a microelectrode device useful for measuring properties of body fluids, those skilled in the art will appreciate that the device will have equal applicability to other fluids, such as those encountered in water pollution monitoring and general chemical analysis. Also, the principles of the followng disclosure need not be limited to microelectrodes, but rather may be adaptable to electrodes of larger dimensions.

Referring to FIG. 2, in one embodiment, the microelectrode device 24 includes a pair of capillary glass tubes 12 intimately contacted, connected, and drawn to form a dual barrel microelectrode device 24. The capillary glass tubes 12 include a shank portion 25 and a tapered portion 30 extending to very fine openings 17. A liquid membrane 11, permeable to both hydrogen ion and carbon dioxide gas is located in the narrow lower tapered portion 30 of each barrel of the dual barrel microelectrode 24. A hydrogen-sensitive fluid 13 is contained in the barrel defining the pH sensor 27, directly above the liquid membrane 11. In the other barrel defining the $P_{CO2}$ sensor, is contained a carbon dioxide-sensitive fluid 14, directly above the liquid membrane 11. Both fluids 13 and 14 are in electrical contact with a dual channel electrometer 23 which measures the voltage signal from each sensor 26 and 27. The electrical contact is supplied by a silver-silver halide wire 16. Although, the particular embodiment described herein refers to a liquid membrane, those skilled in the art will recognize that other types of membranes, solid or liquid, would be equally applicable in the present invention. Examples of other membranes include those prepared from substrates, such as, polyvinylchloride, silicone, and the like.

The reference side of the voltage circuit includes a reference electrode 20 that is in electrical contact with the dual channel electrometer 23 through a potassium chloride/3% agar bridge 19. The agar bridge 19 is connected to the dual channel electrometer 23 by a silver-silver halide wire 16. The reference electrode 20 contacts the fluid sample externally of the microelectrode 24. When the microelectrode 24 is contacting fluid in a body vessel, the reference electrode 20 is preferably fastened to contact the subject's skin or a fluid column in a cannula which contains a portion of the fluid being monitored. If the microelectrode 24 is used in an in vitro sample, the reference electrode 20 may be immersed or otherwise placed in direct ionic contact with the fluid sample.

The dual channel electrometer 23 measures the voltage signal from both sensors 26 and 27. From these voltage signals, the pH and the $P_{CO2}$ of the solution to be tested may be determined. The dual barrel microelectrode device 24 is employed by inserting the small microelectrode openings 17 into the fluid to be monitored. The hydrogen and carbon dioxide present in the fluid to be tested permeates through the liquid membrane 11 into the barrels of sensors 26 and 27. In the barrel, which comprises the pH sensor 27, the hydrogen ion and hydrogen ion sensitive fluid 13 create a voltage signal that is measurable by the electrometer 23. This voltage signal can then be related to the actual pH of the fluid being tested.

In the other barrel, defining the $P_{CO2}$ sensor 26, the $CO_2$ in the test fluid permeates through the liquid membrane 11 and reacts with the $CO_2$ sensitive fluid 14 creating a voltage signal measurable by the electrometer 23. The difference between the voltage signal from the $P_{CO2}$ sensor 26 and the pH sensor 27 can then be related to the actual $P_{CO2}$ of the test fluid.

In another embodiment illustrated in FIG. 1, the microelectrode device of the present invention includes a triple barrel microelectrode 10, that in addition to the pH sensor 27 and the $P_{CO2}$ sensor 26 also includes a $P_{O2}$ sensor 28. The $P_{O2}$ sensor is another glass capillary tube 12, that has a tube shank 25 and a narrow lower tapered portion 30 extending to a very fine microelectrode opening 17. The three glass capillary tubes 12 making up the pH sensor 27, the $P_{CO2}$ sensor 26, and the $P_{O2}$ sensor 28 are intimately contacted and connected to each other to form a small needle-like configuration.

The $P_{O2}$ sensor 28 comprising the capillary glass tube 12 contains in the narrow lower tapered portion 30 the liquid membrane 11 that is permeable to hydrogen ion, carbon dioxide gas and oxygen gas. The other capillary glass tubes making up the $P_{O2}$ and pH sensor also contain the same liquid membrane 11 in the lower narrow tapered portion 30 of the capillary glass tubes 12. In the $P_{CO2}$ sensor 26 and the pH sensor 27 is contained the same carbon dioxide sensitive fluid 14 and hydrogen sensitive fluid 13 as described with relationship to the double barrel microelectrode device 24. In the $P_{O2}$ sensor 28, directly above the liquid membrane 11, is contained an oxygen sensitive fluid 13. This fluid is in electrical contact with a tri-channel electrometer 18 which is also in electrical contact with the hydrogen sensitive fluid 13 and carbon dioxide sensitive fluid 14. The electrical contacts are provided by the silver-silver halide wires 16. The reference side of the tri-channel electrometer 18 includes the same agar bridge 19, and reference electrode 20, as discussed in relation with the dual barrel microelectrode 24.

The tri-channel electrometer 18 measures the voltage signals from each of the $P_{CO2}$ sensor 26, pH sensor 27 and $P_{O2}$ sensor 28. From the voltage signals, the pH, $P_{CO2}$ and $P_{O2}$ of the fluid to be tested may be determined. The triple barrel microelectrode device 10 is employed by inserting the small microelectrode openings 17 into the fluid to be monitored. The pH and $P_{CO2}$ can be determined in the same manner as discussed with regard to the doble barrel microelectrode.

In the barrel defining the $P_{O2}$ sensor 28 the oxygen that permeates through the liquid membrane 11 reacts with the oxygen sensitive fluid to cause a pH change in the fluid of the $P_{O2}$ sensor 28. This pH shift results in a voltage signal which is measured by the tri-channel electrometer. The difference between the voltage signal from the pH sensor 27 and the $P_{O2}$ sensor 28 can then be related to the $P_{O2}$ of the fluid being tested.

Referring to FIG. 3, a microelectrode device 10 in accordance with the present invention is illustrated in a kit form. The microelectrode 10 is packaged in a sterile container 40 which is sealed to prevent contamination of the microelectrode. The microelectrode 10 may further include silver-silver halide wires 16 which are included with the kit. The kit may, though not necessarily, contain instruction for use, (not shown).

Since the dual barrel microelectrode and triple barrel microelectrode device are closely related in their operation and their component parts, the following discussion of the preferred embodiments of the present invention will relate to both embodiments discussed above. That is, the $P_{CO2}$ sensor and pH sensor of the triple barrel microelectrode are very similar to the $P_{CO2}$ and pH sensors of the double barrel microelectrode device.

The capillary tubes which make up the $P_{CO2}$ sensor, pH sensor and the $P_{O2}$ sensor may be fabricated in any manner which insures that the sensors are intimately contacted and connected with each other and drawn to a small enough tip to allow a microelectrode to be used for in vivo type measurement of pH, $P_{CO2}$, and $P_{O2}$. It is preferred that the fabricated microelectrode be of appropriate size and strength to be inserted into body fluid passageways, such as arteries. An example of a method of fabricating such microelectrode employs three single Pyrex glass tubings with outer diameters ranging from about 0.5 to about 2.0 millimeters, preferably about 0.9 millimeters and an inner diameter ranging from about 0.3 to about 1.5 millimeters, preferably about 0.5 millimeters. Such glass tubings are available from the Glass Company of America, Bargain Town, N.J. The glass tubings must be connected in some way, such as gluing them together, twisted under heat, and pulled to a long shank ranging in length from about 1.0 to about 3.0 centimeters, preferably about 2 centimeters. The glass tubing must be connected in a manner that prevents the tubes from dissociating from each other upon heating or twisting. The drawing glass tubings may be then vapor siliconized at about 200° C. in a closed glass jar with tri-N-butylchlorosilane, available from Pfaltz & Bauer, Stanford, Conn.

The formed capillary tubes may then be beveled in the opposite direction to form an arrow like electrode tip with a diameter ranging from about 2 to about 10 micrometers, preferably about 4 to about 6 micrometers. The beveling results in each barrel containing a fine opening at the microelectrode tip ranging in diameter from about 0.5 to about 4.0 micrometers, preferably about 2.0 to about 3.0 micrometers. The arrowlike electrode tip then needs to be thoroughly washed with deionized water and acetone. The triple barrel microelectrode is then in a form which allows for the easy insertion into such things as blood vessels in the human body. It is noted that if the two barrel microelectrode device is desired, only two Pyrex glass tubings are employed.

The liquid membrane may be selected from such materials which are selectively permeable to hydrogen ions and permeable to carbon dioxide gas and oxygen gas. In the case of the double barrel microelectrode, it is only necessary that the liquid membrane be permeable to hydrogen ions but not to other ions and permeable to carbon dioxide gas. Examples of such liquid type membranes include a solution of tri-N-dodecylamine and sodium tetraphenylborate in o-nitrophenyl octyl ether available from 010 WPI, New Haven, Connecticut, and the like. Preferably, the liquid membrane used in the present invention is the solution of tri-N-dodecylamine and sodium tetraphenylborate in o-nitrophenyl octyl ether. The solution preferably comprises 10 g/100 g of the tri-N-dodecylamine and 0.7 g/100 g of sodium tetraphenylborate in the o-nitrophenyl octyl ether. Prior to usage in the present invention, this mixture may be stored overnight under a 100% $CO_2$ atmosphere in a dessicater.

Other types of permeable membranes may be used such as polymeric membranes formed from substrates of polyvinylchloride, silicones, polymethyl methacrylates, polyurethanes, polystyrenes, and the like, which are selectively permeable to hydrogen ions, and permeable to carbon dioxide gas and oxygen gas. It is also possible, where the liquid membrane is used, that thickening stabilizer compositions may be added to the liquid in order to impart a degree of physical integrity to the membrane. Examples of such compositions include hydroxymethyl cellulose, hydroxy ethyl methacrylate and the like.

Since the liquid membrane is selectively permeable to hydrogen, the pH of the test fluid may be measured as a function of the voltage signal generated by the pH sensor. As hydrogen permeates through the liquid membrane into the hydrogen ion responsive fluid, the change in potential may be measured by an electrometer.

Suitable hydrogen ion responsive fluids useful in the practice of the present invention include those fluids which are well buffered and whose pH will not be altered by the presence of carbon dioxide gas or oxygen gas. Examples of such fluids include solutions of sodium citrate-sodium chloride, and the like. Preferably, the fluid filling the pH barrel is a solution of 100 mM sodium citrate-100 mM sodium chloride solution adjusted to a pH of about 6.0.

In order to create a voltage signal in response to the presence of carbon dioxide in the test fluid, it is necessary that the $P_{CO2}$ barrel is filled with a carbon dioxide responsive fluid, capable of interacting with carbon dioxide in such a manner that causes a measurable change in the hydrogen ion content (i.e., pH) of the fluid in the carbon dioxide sensor. Examples of such carbon dioxide responsive fluids include solutions of sodium bicarbonate-sodium chloride, and the like. Preferably, the carbon dioxide responsive fluid is a solution of 20 mM sodium bicarbonate-100 mM sodium chloride.

As carbon dioxide in the test fluid permeates through the liquid membrane into the carbon dioxide responsive fluid a shift will occur in the equilibrium of the carbon dioxide responsive fluid which results in a change of the hydrogen ion content (i.e., pH) of the carbon dioxide responsive fluid. This change in hydrogen ion concentration is measurable as a voltage signal. Under equilibrium conditions, the partial pressure of carbon dioxide will be the same on both sides of the liquid membrane. Therefore, variations of the partial pressure of carbon dioxide outside the microelectrode will originate equal variations of the partial pressure of carbon dioxide in the carbon dioxide responsive fluid. In a preferred embodiment, the increase of hydrogen ion concentration of the CO$_2$ sensitive fluid may be represented by the following formulas:

$$CO_2 + H_2O \rightarrow H_2CO_3$$

$$H_2CO_3 \rightarrow H^+ + HCO_3$$

Since the liquid membrane is also permeable to oxygen, it is possible to create a voltage signal in the oxygen sensor in a manner similar to the way a voltage signal is created in the carbon dioxide sensor. Since, under equilibrium conditions, the partial pressure of O$_2$ will be the same on both sides of the liquid membrane, variations of the partial pressure of O$_2$ outside the membrane will originate equal variations of the partial pressure of O$_2$ in the oxygen responsive fluid. Therefore, it is necessary to choose an oxygen responsive fluid which is capable of changing the hydrogen ion content and/or pH of the O$_2$ responsive fluid when the oxygen responsive fluid comes into contact with additional amounts of oxygen. The change in the hydrogen ion content and/or pH of the oxygen responsive fluid may be the result of a shift in the equilibrium of the oxygen responsive fluid. This change in the hyrogen ion content and/or pH results in the creation of a voltage signal which is measurable by an electrometer.

Examples of suitable oxygen responsive fluid useful in the present invention include aqueous solutions of iron sulphate salt (FeSO$_4$) and extensively deoxygenated water, solutions of glucose and deoxygenated water, solutions of reduced nicotinamide adenine dinucleotide, and solutions of hemoglobin dissolved in deoxygenated water. Preferably, the oxygen responsive fluid is an iron sulfate salt (FeSO$_4$) used in amounts of about $1 \times 10^{-3}$M.

The increase or decrease in hydrogen ion content and/or pH of the oxygen responsive fluid may be represented by a number of formulas listed below:

1. Oxidation of Ferrous Ion (Fe$^{2+}$)

$$4Fe^{+2} + O_2 + 4H^+ \rightleftharpoons 4Fe^{3+} + 2H_2O$$

$$Fe^{3+} + 3H_2O \rightleftharpoons Fe(OH)_3 + 3H^+$$

2. Oxidation of glucose $$glucose + H_2O + O_2 \underset{}{\overset{glucose\ oxidase}{\rightleftharpoons}} gluconic\ acid + H_2O_2$$

3. Oxidation of Reduced Nicotinamide Adenine Dionucleotide $$2(NADH) + O_2 + 2H^+ \xrightarrow[\text{Horseradish Peroxidase}]{} 2NAD^+ + 2H_2O$$

4. Hemoglobin (Bohr effect)
Hemoglobin$-H^+ + O_2 \rightarrow$ Hemoglobin$-O_2 + H^+$ A change in the hydrogen ion content and/or pH in any of the sensitive liquids described hereinabove results in a change in the voltage signal created by the sensitive fluid. Each of the sensitive fluids in the microelectrode sensors is connected electrically to a voltage signal measuring device. The fluids are connected to such device by wires of silver-silver halide, and the like conventionally used in the art of electrode devices. Preferably, silver-silver halide wires are employed in the practice of the present invention.

The device which is used to measure the volage signal may be any device in conventional use for such purpose. Examples of such devices include double and triple channel high impedance electrometers, such as Model FD-223, available from WPI, New Haven, CT. The choice of the particular device used to measure the voltage signal is not critical to the practice of the present invention.

The voltage signal of the hydrogen, carbon dioxide, oxygen sensitive fluids in the microelectrode device barrels is determined with reference to a conventional reference electrode. The reference electrode may be any of a number known in the art. Preferably, the reference electrode is a silver-silver halide electrode which contacts the fluid sample externally of the microelectrode. The reference electrode is in electrical communication with the electrometer via a conventional agar bridge, such as a 3M potassium chloride in 3% agar bridge. The reference electrode serves to complete the electrical circuit so therefor must be placed in ionic contact with the fluid being tested. When the microelectrode is in a body vessel, the reference electrode is preferably fastened to contact the subject's skin or a fluid column in a cannula. If the microelectrode is being used in an in vitro sample, the reference electrode may be immersed or otherwise in direct ionic communication with the fluid sample. The voltage signal and voltage differences between each channel may be monitored with a conventional digital meter and recorder available from Gould.

When the liquid membrane is used, the microelectrode device of the present invention is fabricated by filling each of the barrels of the microelectrode with the respective hydrogen, carbon dioxide, or oxygen sensitive fluid and the liquid membrane. This may be done by back filling the thoroughly clean barrel with the particular sensitive fluid and then aspirating a column of the liquid membrane into the tip of the barrel. Prior to aspirating the liquid membrane into the other tips of the microelectrode device, it is preferred that a few drops of the sensitive fluid be pushed out through the tip to wash off any prior contamination with the solution from the other barrels. The liquid membrane may then be aspirated into each of the remaining two barrels.

The amount of liquid membrane which is apirated into each individual barrel may be dependent upon the particular type of sensor the barrel is used as. It is preferred that the column of liquid membrane be adjusted to a height ranging from about 150 to 250 micrometers in each barrel. It is noted that for most measurements the electrodes with equal amounts of liquid membrane columns would be satisfactory.

The microelectrode device of the present invention may be configured in two embodiments. In one preferred embodiment, the microelectrode may contain three barrels, one for measuring pH, one for P$_{CO2}$ and one for P$_{O2}$. In another preferred embodiment, it is possible that only a two barrel system be configured in which one barrel measures the pH and one barrel measures the P$_{CO2}$.

Due to the small size of the tips of the microelectrode devices of one embodiment of the present invention, it is possible that the devices be used for the in vivo measurement of properties of body fluids. The microelectrode device of the present invention is very simple to use and easy to fabricate which will result in a low cost of production and availability of a disposable microelectrode device.

In the electrode device of the present invention, one barrel is used as a pH electrode. In determining the $P_{CO2}$ and $P_{O2}$, the pH barrel and the respective $P_{CO2}$ or $P_{O2}$ barrel is used to determine the $P_{CO2}$ or $P_{O2}$. Due to the slope of relationship of the Nernst equation represented by:

$$E'_{H+} = S \log_{10} [H^+]_o/[H^+]'_i + E_o' \text{ pH response} \quad (1)$$

$$E''_H = S \log_{10} [H^+]_o/[H^+]''_i + E_o'' \, P_{CO2} \text{ or } P_{O2} \text{ response} \quad (2)$$

wherein S is the slope of the electrode response and should be theoretically the same for both sides. $E_o$ is the standard electrode voltage and includes all liquid junction potentials in the circuit, and $[H^+]_o$ and $[H^+]_i$ are the hydrogen ion concentrations in the solution tested and the solution filling each barrel, respectively. By subtracting the two equations and assuming that S is the same for each barrel, it is possible to develop a relationship that would predict that the difference between the voltage measured between the pH and the $P_{CO2}$ barrel would be a logarithmic function of the $P_{CO2}$ with a Nernstian slope represented by the formula:

$$\Delta E - \Delta E_o = S \log_{10} ([H^+]''_i/[H^+]'_i) \quad (3)$$

from which one obtains the following, by combining equation 3 with a rearrangement of the Henderson-Hasselbalch equation represented by the formula:

$$P_{CO2} = [HCO_3^-]''_i [H^+]''_i / 0.0301K \quad (4)$$

to give $$E_{PCO2} = \Delta E - \Delta E_o = S \log_{10} [P_{CO2}] + A \quad (5)$$

wherein K is the dissociation constant and $[HCO_3^-]''_i$ is the bicarbonate concentration in the carbon dioxide responsive fluid which would be virtually unaffected by $P_{CO2}$, and $$A = -S \log_{10} ([HCO_3^-]''_i [H^+]'_i / 0.0301K) + \Delta E_o. \quad (6)$$

A similar relationship exists for the $P_{O2}$ barrel and may be represented by the equation:

$$E_{PO2} = \Delta E - \Delta E_o = S \log_{10} [f(P_{O2})] + A' \quad (7)$$

wherein $A' = -S \log_{10} [H^+]_i + \Delta E_o$ and $f(P_{O2})$ is dependent on the particular oxygen sensitive fluid used.

Therefore, in using the present invention, it would be possible to determine the pH directly, the $P_{O2}$ by the difference in the voltage potential between the pH and the $P_{O2}$ barrels, and the $P_{CO2}$ by determining the voltage difference between the pH barrel and the $P_{CO2}$ barrel.

Therefore, the present invention provides a most attractive device for measuring the pH, $P_{CO2}$, and $P_{O2}$ properties of body fluids and other fluids by the use of an electrode which may simultaneously measure such properties. The other useful feature of the electrode device is that it is simple and quick to fabricate.

The foregoing components are easily adaptable to being supplied in a kit form for practicing in vitro or in vivo type pH, $P_{CO2}$, and $P_{O2}$ measurements. A representative kit would include a formed triple or double barrel microelectrode in accordance with one embodiment of the presently described invention. The microelectrode may or may not be loaded with the sensitive fluids and the membrane. When the capillary tubes have been loaded with this sensitive fluid and the membrane, care should be taken that the open portions of the microelectrode device be sealed in order to prevent the leaking of such fluids. It may be preferred to include with the kit the electrical connections which may be connected to conventional types of voltage measuring devices. All of the above kit components will be packaged in one or more sterile packets and will typically, but not necessarily, be sold with printed instructions for the use of the present invention.

Although the present invention has been described with regards to a particular embodiment which employs glass capillary tubes as sensor means, the scope of the present invention is not to be limited to only glass microelectrodes. It is possible that the capillary tubes may be prepared from other polymeric materials of greater mechanical strength which are compatible with in vivo and in vitro applications, such as plastics, rubbers, ceramics, and the like.

The following examples are intended to illustrate embodiments of the present invention and are not intended to limit the scope in any way.

EXAMPLE 1

To illustrate the practice of one embodiment of the present invention, a double barrel microelectrode is prepared in the following manner. Two single Pyrex glass tubings with OD 0.9 millimeters, and ID 0.5 millimeters available from the Glass Company of America, Bargain Town, N.J., are glued together, twisted under heat, and pulled to a long shank of about 2 centimeters. The capillary glass tubes thus formed are then vapor siliconized at 200° C. in a closed glass jar with 2 microliters of tri-N-butylchlorosilane available from Pfaltz & Bauer, Stanford, Conn.

Each individual barrel is beveled in the opposite direction to form an arrow-like electrode tip with a diameter of 4–6 micrometers. After a thorough wash with iodized water and acetone, the $P_{CO2}$ barrel is filled with a Millipore filter unit with 20 mM sodium bicarbonate-100 mM sodium chloride solution and then a column of 10 g/100 g of liquid tri-N-dodecylamine and 0.7 g/100 g of sodium tetraphenylborate in o-nitrophenyl octyl ether available from 010 WPI, New Haven, Conn., is aspirated into the tip. The pH barrel is then back filled through a filter with 100 mM sodium citrate-100 mM sodium chloride solution adjusted to a pH of about 6.0. A few droplets of this solution is pushed out through the tip to wash off any prior contamination with a solution from the other barrel, and the liquid membrane is then aspirated into this barrel. The liquid membrane is aspirated into each barrel to a height of about 200 micrometers in each barrel. The $P_{CO2}$ response was 54 mV/$\log_{10} P_{CO2}$, and the pH was 58 mV/pH unit at 20° C. Each barrel was connected through a silver-silver chloride wire to a dual channel (A and B) high impedance electrometer (Model FD-223, WPI, New Haven, Conn.). A 3M potassium chloride solution in 2% agar bridge is used as the reference side of the circuit. The voltage signal from the pH barrel (channel A, $E_{H+}$) and the reading of the voltage difference between the two channels (A-B), $\Delta E = E_{PCO2}$ is monitored with a digital meter and a recorder available from Gould, Inc., Recording Systems, Cleveland, OH. Because the $P_{CO2}$ voltage response is measured as a voltage difference between the two barrels, the liquid junction potential of the 3M potassium chloride agar bridge will not affect the $P_{CO2}$ measurements. For the pH measurements, it is estimated that the differences in junction potentials, when making solution changes, is too small to affect the pH voltage response. The electrode resistances are $10^{10}$–$10^{11}$ ohms.

To evaluate the performance of the pH-$P_{CO2}$ microelectrode in solutions containing either $HCO_3$, $NO_3$, $SO_4$, or N-2-hydroxyethylpiperazine-N'-ethanesulfonate (HEPES), the solutions are extensively bubbled with 10% $CO_2$-90% $O_2$ gas mixture. The pH measurements with the microelectrode compared favorably with a commercial pH macroelectrode (Model 12, Corning) for all solutions except the $NO_3$ solution. With the $NO_3$ in the solution, the microelectrode measured a pH value 0.19 pH units higher. The $P_{CO2}$ voltage response was virtually identical regardless of the type of anion present in the solutions tested. The results are reported in Table 1 and Table 2.

TABLE 1

| | SOLUTION | | | |
|---|---|---|---|---|
| | $HCO_3$ | $NO_3$ | $SO_4$ | HEPES |
| MICROELECTRODE | 7.22 | 5.58 | 5.41 | 7.14 |
| MACROELECTRODE* | 7.26 | 5.39 | 5.38 | 7.18 |

*Not an example of the present invention. Each solution contained 30 mM of the anion and 120 mM NaCl.

TABLE 2

| | SOLUTION | | | |
|---|---|---|---|---|
| | $HCO_3$ | $NO_3$ | $SO_4$ | HEPES |
| $E_{PCO2}$, mV | −71 | −71 | −72 | −72 |

The data reported in Table 1 illustrates the effectiveness of the present invention in accurately measuring the pH value of various fluids. The data of Table 2 illustrates that the $P_{CO2}$ voltage response is unaffected by the type of particular ion, which is present in the solution to be monitored.

EXAMPLE 2

Using a microelectrode device prepared in the same manner as described in Example 1, measurements of the pH-$P_{CO2}$ in the arterial blood and serum from rats is compared with values obtained with a macroelectrode (Model ABL 1, Radiometer).

In vivo measurements are performed in renal proximal tubules and peritubular capillaries of SPRAGUE-DAWLEY rats that are prepared for micropuncture as described in Bomstyk, K., J. P. George, and F. S. Wright; Effects of Luminal Fluid Anions on Calcium Transport By Proximal Tubule. AM. J. PHYSIOL. 246 (Renal Fluid Electrolyte Physiol. 15): F600-F608, 1984. The surface of the kidney is bathed with a solution containing in mM, Na, 140; Cl, 114; $HCO_3$, 30; and K, 4.0, and is warmed to 37° C. Measurements of pH-$P_{CO2}$ in tubules and adjacent capillaries is done in pairs, and the order is alternated. To minimize the effect of the electrode drift, each pair of measurements is bracketed between two different calibration solutions, and readings are taken once voltage response is stable.

The calibration solutions contained 20 mM sodium bicarbonate and 130 mM sodium chloride bubbled with either 3% or 10% carbon dioxide gas mixture maintained at 37° C. The $P_{CO2}$ in the calibration solutions is determined by both macroelectrode (Model ABL 1, Radiometer) and calculated from measured pH (Model 12, Corning) and known $HCO_3$ concentration. $P_{CO2}$ in the tissue/body fluid is determined using the equation:

$$P_{CO2} = P'_{CO2} \exp_{10}[(E_{PCO2} - E'_{PCO2})/S]$$

where $P'_{CO2}$ is the known $CO_2$ tension in either one of the calibration solutions, $E_{PCO2}$ and $E'_{PCO2}$ is the difference between the voltage with each barrel in the tissue/body fluid and in the calibration solution. S is the slope of the $P_{CO2}$ voltage response calculated from:

$$S = (E'_{PO2} - E''_{PCO2})/\log_{10}(P'_{CO2}/P''_{CO2})$$

where $P'_{CO2}$ and $P''_{CO2}$ are the known $CO_2$ tensions and $E'_{PCO2}$ and $E''_{PCO2}$ are the $P_{CO2}$ voltage readings in the two calibration solutions.

The tissue/body fluid pH is determined from the equation:

$$pH = (E'_{H+} - E_{H+})/S^* + pH'$$

where $pH'$ is the known pH of either one of the calibration solutions and $E_{H+}$ and $E'_{H+}$ are the pH electrode voltage readings in the tissue/body fluid and in the calibration solution, respectively. $S^*$ is the slope of the pH electrode calculated from:

$$S^* = (E'_{H+} - E''_{H+})/(pH'' - pH')$$

where $pH''$ and $pH'$ are the known pH and $E''_{H+}$ and $E'_{H+}$ are the pH voltage readings in the two calibration solutions.

Collections of the proximal tubule fluid are performed in standard fashion into micropipettes containing mineral oil equilibrated with 7% $CO_2$—93% $O_2$. The results of the measurements using both the microelectrode and the macroelectrode are reported in Table 3 as average values of a number of runs illustrated by the number in parenthesis.

TABLE 3

| | $P_{CO2}$, mmHg | pH |
|---|---|---|
| ARTERIAL BLOOD | | |
| MICROELECTRODE | 37.4 ± 2.7 (14) | 7.34 ± 0.04 (14) |
| MACROELECTRODE* | 39.4 ± 3.0 (14) | 7.30 ± 0.02 (14) |
| ARTERIAL SERUM | | |
| MICROELECTRODE | 28.9 ± 3.7 (14) | 7.59 ± 0.05 (14) |
| MACROELECTRODE* | 29.7 ± 2.8 (14) | 7.58 ± 0.05 (14) |

*Not an example of the present invention.

The data in Table 3 illustrates the accuracy of the present invention when used for the in vivo measurements of pH and $P_{CO2}$ in fluid passageways of the body.

The embodiments of the invention in which an exclusive property or privilege is claimed are defined as follows:

1. An electrode device capable of simultaneously measuring pH and $P_{CO2}$ comprising:
    (a) means defining a pH sensor, said pH sensor comprising a hydrogen ion and carbon dioxide gas permeable membrane in contact with a hydrogen ion responsive fluid, said fluid capable of being placed in contact with a means for measuring the voltage signal from the pH sensor;

(b) means defining a $P_{CO2}$ sensor, said $P_{CO2}$ sensor comprising a hydrogen ion and carbon dioxide permeable membrane having the same composition as the membrane in (a) in contact with a carbon dioxide responsive fluid, said fluid capable of being placed in contact with a means for measuring the voltage signal from the $P_{CO2}$ sensor; and (c) wherein the means defining the pH sensor and the means defining the $P_{CO2}$ sensor are connected to each other.

2. The electrode device of claim 2, wherein said hydrogen ion and carbon dioxide gas permeable membrane is a liquid membrane consisting of tri-N-dodecylamine and sodium tetraphenylborate in o-nitrophenyl octyl ether.

3. The electrode device of claim 1, wherein said hydrogen ion responsive fluid is a solution consisting of sodium citrate/sodium chloride.

4. The electrode device of claim 1, wherein the means for measuring the voltage comprises a silver-silver chloride wire.

5. The electrode device of claim 1, wherein the carbon dioxide responsive fluid is a solution consisting of sodium bicarbonate/sodium chloride.

6. The electrode device of claim 1, wherein the means defining the pH sensor comprises a capillary tube.

7. The electrode device of claim 1, wherein the means defining the $P_{CO2}$ sensor comprises a capillary tube.

8. The device of claim 6 or 7, wherein the hydrogen ion and carbon dioxide gas permeable liquid membrane is a solution of o-nitrophenyl octyl ether containing about 10 g/100 g of tri-N-dodecylamine and about 0.7 g/100 g of sodium tetraphenylborate.

9. The electrode device of claim 8, wherein the hydrogen ion responsive fluid is a solution containing about 100 mM sodium citrate — 100 mM sodium chloride.

10. The electrode device of claim 9, wherein the carbon dioxide responsive fluid is a solution containing about 20 mM sodium bicarbonate — 100 mM sodium chloride.

11. The electrode device of claim 6, wherein the hydrogen ion and carbon dioxide gas permeable liquid membrane is used in an amount sufficient to occupy the lower portion of the capillary tube ranging in length from about 150 to about 250 microns.

12. The electrode device of claim 7, wherein the hydrogen ion and carbon dioxide gas permeable liquid membrane is used in an amount sufficient to occupy the lower portion of the capillary tube ranging in length from about 150 to about 250 microns.

13. The electrode device of claim 1, wherein the hydrogen ion responsive fluid is in contact with a means for measuring the voltage signal from the pH sensor.

14. The electrode device of claim 1, wherein the carbon dioxide ion responsive fluid is in contact with a means for measuring the voltage signal from the $P_{CO2}$ sensor.

15. The electrode device of claim 1, wherein the hydrogen ion and carbon dioxide gas permeable membrane comprises substrates selected from the group consisting of polyvinylchloride, silicones, polymethyl methacrylate, polyurethanes, and polystyrenes.

16. An electrode kit useful for simultaneously measuring pH and $P_{CO2}$ comprising sterile packaging and the electrode device of claim 1.

17. The electrode kit of claim 16, further comprising a pair of silver-silver halide wires.

18. The electrode kit of claim 17, further comprising instructions for use.

19. An electrode device for simultaneously measuring pH, $P_{CO2}$, and $P_{O2}$ comprising:

(a) means defining a pH sensor, said pH sensor comprising a hydrogen ion, carbon dioxide gas, and oxygen gas permeable membrane in contact with a hydrogen ion responsive fluid, said fluid capable of being placed in contact with a means for measuring the voltage signal from the pH sensor;

(b) means defining a $P_{CO2}$ sensor comprising a hydrogen ion, carbon dioxide gas and oxygen gas permeable membrane having the same composition as the membrane in (a) in contact with a carbon dioxide responsive fluid, said fluid capable of being placed in contact with a means for measuring the voltage signal from the $P_{CO2}$ sensor;

(c) means defining a $P_{O2}$ sensor, said $P_{O2}$ sensor comprising a hydrogen ion, carbon dioxide gas, and oxygen gas permeable membrane having the same composition as the membranes in (a) and (b) in contact with an oxygen responsive fluid, said fluid capable of being placed in contact with a means for measuring the voltage signal from the $P_{O2}$ sensor; and (d) wherein the means defining the pH sensor, the means defining the $P_{CO2}$ sensor, and the means defining the $P_{O2}$ sensor are connected to each other.

20. The electrode device of claim 19, wherein said hydrogen ion, carbon dioxide gas and oxygen gas permeable membrane is a solution consisting of tri-N-dodecylamine and sodium tetraphenylborate in o-nitrophenyl octyl ether.

21. The electrode device of claim 20, wherein the means defining the pH sensor comprises a capillary tube.

22. The microelectrode device of claim 21, wherein the hydrogen ion, carbon dioxide gas, and oxygen gas permeable liquid membrane is used in an amount sufficient to occupy the lower portion of the capillary tube ranging in length from about 150 to about 250 microns.

23. The electrode device of claim 20, wherein the means defining the $P_{CO2}$ sensor comprises a capillary tube.

24. The microelectrode device of claim 23, wherein the hydrogen ion, carbon dioxide gas, and oxygen gas permeable liquid membrane is used in an amount sufficient to occupy the lower portion of the capillary tube ranging in length from about 150 to about 250 microns.

25. The electrode device of claim 20, wherein the means defining the $P_{O2}$ sensor comprises a capillary tube.

26. The microelectrode device of claim 25, wherein the hydrogen ion, carbon dioxide gas, and oxygen gas permeable liquid membrane is used in an amount sufficient to occupy the lower portion of the capillary tube ranging in length from about 150 to about 250 microns.

27. The electrode device of claim 20, wherein the hydrogen ion, carbon dioxide gas and oxygen gas permeable liquid membrane is a solution of o-nitrophenyl octyl ether containing about 10 grams/100 grams of tri-N-dodecylamine and about 0.7 grams/100 grams of sodium tetraphenylborate.

28. The electrode device of claim 27, wherein the hydrogen ion responsive fluid is a solution containing about 100 mM sodium citrate-100 mM sodium chloride.

29. The electrode device of claim 28, wherein the carbon dioxide responsive fluid is a solution containing about 20 mM sodium bicarbonate-100 mM sodium chloride.

30. The microelectrode device of claim 29, wherein the oxygen responsive fluid is a solution of about $1.0 \times 10^{-3}$ M iron sulfate salt dissolved in water.

31. The electrode device of claim 19, wherein said hydrogen ion responsive fluid is a solution consisting of sodium citrate/sodium chloride.

32. The electrode device of claim 19, wherein the means for measuring the voltage comprises a silver-silver chloride wire.

33. The electrode device of claim 19, wherein the carbon dioxide responsive fluid is a solution of sodium bicarbonate/sodium chloride.

34. The electrode device of claim 19, wherein the oxygen responsive fluid is a solution containing at least one component selected from the group consisting of ferrous ion, glucose/glucose oxidase, reduced nicotinamide adenin dinucleotide, and hemoglobin.

35. The electrode device of claim 19, wherein the hydrogen ion responsive fluid is in contact with a means for measuring the voltage signal from the pH sensor.

36. The electrode device of claim 19, wherein the carbon dioxide ion responsive fluid is in contact with a means for measuring the voltage signal from the $P_{CO2}$ sensor.

37. The electrode device of claim 19, wherein the oxygen ion responsive fluid is in contact with a means for measuring the voltage signal from the $P_{O2}$ sensor.

38. The electrode device of claim 19, wherein the hydrogen ion, carbon dioxide gas and oxygen gas permeable membrane comprises substrates selected from the group consisting of polyvinylchloride, silicones, polymethyl methacrylate, polyurethanes, and polystyrenes.

39. An electrode kit useful for simultaneously measuring pH, $P_{CO2}$, and $P_{O2}$ comprising sterile packaging and the microelectrode device of claim 19.

40. The electrode kit of claim 39, further comprising a pair of silver-silver halide wires.

41. The electrode kit of claim 39, further comprising instructions for use.

42. The electrode device of claim 1 or 19, wherein the hydrogen ion responsive fluid is a buffered solution whose pH is not affected by the presence of carbon dioxide gas or oxygen gas.

43. The electrode device of claim 1 or 19, wherein the pH of the carbon dioxide responsive fluid changes in response to a change in the $P_{CO2}$ of the carbon dioxide responsive fluid.

44. The electrode device of claim 19, wherein the pH of the oxygen sensitive responsive fluid changes in response to a change in the $P_{O2}$ of the oxygen responsive fluid.

* * * * *

UNITED STATES PATENT AND TRADEMARK OFFICE
CERTIFICATE OF CORRECTION

PATENT NO. : 4,816,131

DATED : March 28, 1989

INVENTOR(S) : Karol Bomsztyk

It is certified that error appears in the above-identified patent and that said Letters Patent is hereby corrected as shown below:

| Column | Line | |
|---|---|---|
| 2 | 1 | "presnt" should be --present-- |
| 2 | 49 | "volage" should be --voltage-- |
| 2 | 52 | "arbon" should be --carbon-- |
| 3 | 18 | "FIG. 1" should be --FIG. 2-- |
| 3 | 22 | "FIG. 2" should be --FIG. 1-- |
| 3 | 41 | "FIG. 2" should be --FIG. 1-- |
| 4 | 34 | "FIG. 1" should be --FIG. 2-- |
| 5 | 6 | "doble" should be --double-- |
| 5 | 22 | "use," should be --use-- |
| 5 | 56 | "Stanford" should be --Stamford-- |
| 8 | 7 | "volage" should be --voltage-- |
| 8 | 27 | "therefor" should be --therefore-- |
| 10 | 45 | "Stanford" should be --Stamford-- |
| 13 | 14 | "2" should be --1-- |
| 14 | 44 | "microelectrode" should be --electrode-- |
| 14 | 52 | "microelectrode" should be --electrode-- |
| 14 | 60 | "microelectrode" should be --electrode-- |
| 15 | 10 | "microelectrode" should be --electrode-- |

Signed and Sealed this

Ninth Day of January, 1990

*Attest:*

JEFFREY M. SAMUELS

*Attesting Officer*     *Acting Commissioner of Patents and Trademarks*